US009993311B2

(12) United States Patent
Koudijs et al.

(10) Patent No.: US 9,993,311 B2
(45) Date of Patent: Jun. 12, 2018

(54) VISUALIZING SURGICAL TRAJECTORIES (75) Inventors: Johannes Cornelis Koudijs, Eindhoven (NL); Martin Bergtholdt, Hamburg (DE); Heinrich Schulz, Hamburg (DE); Hubert Cecile Francois Martens, Eindhoven (NL); Gerrit-jan Bloem, Eindhoven (NL); Johan Gerard Kleibeuker, Helvoirt (NL)

(73) Assignee: Koninklijke Philips N.V., Eindhoven (NL)

( * ) Notice: Subject to any disclaimer, the term of this patent is extended or adjusted under 35 U.S.C. 154(b) by 239 days.

(21) Appl. No.: 13/383,671

(22) PCT Filed: Jul. 13, 2010

(86) PCT No.: PCT/IB2010/053198
§ 371 (c)(1),
(2), (4) Date: Jan. 12, 2012

(87) PCT Pub. No.: WO2011/007318
PCT Pub. Date: Jan. 20, 2011

(65) Prior Publication Data
US 2012/0120091 A1    May 17, 2012

(30) Foreign Application Priority Data
Jul. 15, 2009 (EP) .................................. 09165513

(51) Int. Cl.
*A61B 34/10* (2016.01)
*A61B 90/10* (2016.01)
*A61B 34/20* (2016.01)

(52) U.S. Cl.
CPC .............. *A61B 90/10* (2016.02); *A61B 34/10* (2016.02); *A61B 34/20* (2016.02); *A61B 2034/107* (2016.02)

(58) Field of Classification Search
None
See application file for complete search history.

(56) References Cited

U.S. PATENT DOCUMENTS

| 3,888,260 A | 6/1975 | Fischell |
| 4,431,001 A | 2/1984 | Hakansson et al. |

(Continued)

FOREIGN PATENT DOCUMENTS

| JP | 2000333971 A | 12/2000 |
| JP | 2003030624 A | 1/2003 |
| WO | 2011007318 A1 | 1/2011 |

OTHER PUBLICATIONS

Viard, Romain, et al., Needle Positioning in Interventional MRI Procedure: Real Time Optical Localisation and Accordance With the Roadmap. Proceedings of the 29th Annual International Conference of the IEEE EMBS, Lyon, France, August 23-26, 2007. pp. 2748-2751.

(Continued)

*Primary Examiner* — Xiao Wu
*Assistant Examiner* — Steven Elbinger (57) ABSTRACT A method and system are provided for visualizing a surgical path for a surgical tool. The method comprises a step of receiving anatomical information about a position of at least one anatomical structure in a region to undergo surgery, geometric information describing the surgical path and at least one safety margin defining a minimal distance between the surgical tool and the anatomical structure. The method further comprises defining a critical segment of the surgical path, in which critical segment a distance to the anatomical structure is smaller than the safety margin. Then a graphical representation of the surgical path is provided, wherein the critical segment is highlighted.

12 Claims, 9 Drawing Sheets (56) References Cited

U.S. PATENT DOCUMENTS

| | | | |
|---|---|---|---|
| 5,638,819 A | 6/1997 | Manwaring et al. | |
| 6,671,538 B1 | 12/2003 | Ehnholm et al. | |
| 6,842,639 B1* | 1/2005 | Winston et al. | 600/478 |
| 7,211,351 B2 | 5/2007 | Klaassen | |
| 7,337,010 B2 | 2/2008 | Howard et al. | |
| 7,496,404 B2 | 2/2009 | Meadows et al. | |
| 2006/0142657 A1* | 6/2006 | Quaid | A61N 1/372 600/424 |
| 2006/0184029 A1* | 8/2006 | Haim et al. | 600/443 |
| 2007/0049861 A1* | 3/2007 | Gundel | 604/27 |
| 2007/0197896 A1* | 8/2007 | Moll | A61B 1/00039 600/407 |
| 2007/0244387 A1* | 10/2007 | Rodriguez Ponce et al. | 600/411 |
| 2008/0071292 A1 | 3/2008 | Collin | |
| 2011/0004059 A1* | 1/2011 | Arneson et al. | 600/109 |
| 2012/0120091 A1 | 5/2012 | Koudijs | |

OTHER PUBLICATIONS

Hagmann, E., et al. A Haptic Guidance Tool for CT-Directed Percutaneous Interventions. Annual International Conference of the IEEE EMBS, Sep. 1-5, 2004, p. 2746-2749.

\* cited by examiner

VISUALIZING SURGICAL TRAJECTORIES

FIELD OF THE INVENTION

This invention relates to a method of visualizing a surgical path for a surgical tool, the method comprising receiving anatomical information about a position of at least one anatomical structure in a region to undergo surgery and geometric information describing the surgical path.

This invention further relates to a system and a computer program product for performing such a method.

BACKGROUND OF THE INVENTION

From United States patent application US 2007/0049861 A1 a system is known for automated planning of an access path for a minimally invasive intervention of an area of the body. 3D image data of the body area is processed and bones and elements endangered by the intervention are segmented. The image data is displayed and the user marks a target position in the image. The system then automatically determines one or more access paths to the target position which do not run through bones and which do not intersect any elements endangered by the intervention. The one or more access paths are then presented to a user on a monitor and the user can interactively select and/or correct an access path. If no suitable path is found, the user is presented with alternatives in which injuries to the structures cannot be excluded. The endangered structures are highlighted to help the user with making an informed decision.

The known US patent application thus describes a planning system providing two kinds of information, i.e. safe surgical paths not intersecting with any important structure and unsafe paths intersecting at least one important structure. In addition to the unsafe path, the system indicates the structures harmed by the unsafe path. One of the disadvantages of the known system is that it can only be used for deciding, during planning of the surgery, which anatomical structure is going to be damaged. It does not provide a practical solution for a surgeon who wants to optimize the surgical path before as well as during surgery.

OBJECT OF THE INVENTION

It is an object of the invention to provide a method of visualizing a surgical path as described in the opening paragraph, which method makes it easier to avoid damage of critical anatomical structures.

SUMMARY OF THE INVENTION

According to a first aspect of the invention, this object is achieved by providing a method of visualizing a surgical path for a surgical tool, the method comprising receiving anatomical and geometric information and at least one safety margin, defining a critical segment and providing a graphical segment of the surgical path. The anatomical information describes a position of at least one anatomical structure in a region to undergo surgery. The geometric information describes the surgical path. The safety margin defines a minimal distance between the surgical tool and the anatomical structure. The critical segment is highlighted in the graphical representation of the surgical path. In the critical segment a distance to the anatomical structure is smaller than the safety margin.

With the method according to the invention, the path's critical information is provided in an easily interpretable and easily accessible way. Where the path tends to come to close to an important anatomical structure, it is highlighted. A user can easily see whether a path comprises critical segments. Especially in cases with complicated 3D anatomical geometry this allows a user to very quickly assess which part of a selected or proposed trajectory bears a risk related to a specific structure. The user may then decide to look for another route to the target point or may accept the risk of damaging tissue (and act extremely careful) at the highlighted segment. Highlighting critical segments may, e.g., be done using color coding or different shades or by drawing circles or other shapes around the critical segments. It is to be noted that the method according to the invention may be used for planning a surgical trajectory as well as for following a surgical tool during surgery.

This provides a large advantage of the prior art system described in US2007/0049861. If the prior art system finds a path which does not intersect any structure but comes very close to a critical anatomical structure, the surgeon will not recognize that. A small deviation from the planned surgical path during surgery may have very dramatic consequences. In contrast, the system according to the invention may easily inform the surgeon when a path comes very close to a critical structure.

In a preferred embodiment the method further comprises receiving at least one surgical tool restriction, defining a restricted segment of the surgical path, in which restricted segment the surgical path does not meet the surgical tool restriction, and highlighting the restricted segment in the graphical representation of the surgical path.

The possible paths for a surgical tool travelling towards a target point, may not only be restricted by critical anatomical structures laying in the way. The surgical tool may, e.g., not be suitable for turning sharp corners or for turning to many corners on a too short path segment. Furthermore, the total path length may be limited. Such restrictions may be taken into account when graphically representing the surgical path. Highlighting restricted segments may, e.g., be done using color coding or different shades or by drawing circles or other shapes around the restricted segments.

The method according to the invention preferably also comprises steps of receiving an image of a region to undergo surgery, and displaying the image together with the graphical representation of the surgical path. This enables the user to have a clear overview of all anatomical details as provided by the images and to assess the important aspects of the surgical path simultaneously. The highlighting of path segments instead of the anatomical structures (like in US 2007/0049861 A1) has as an additional advantage that no important details of the critical anatomical structures are obscured. The anatomical information may be received from an external source, but is preferably derived from the images using image recognition techniques.

The graphical representation of the surgical path may be aligned with and displayed upon the image of the region to undergo surgery or may be displayed separately. For example, the graphical representation of the surgical path comprises a bar, both ends of the bar representing a first point and a second point on the surgical path, a position on the bar in between the ends representing a corresponding position on the surgical path in between the first point and the second point. Such a one dimensional representation of the surgical path may not give a clear overview of the geometric course of the surgical tool, but does provide important information about what risks and other problems are to be expected as the surgical tool is moved towards the target point. In a preferred embodiment, this bar representation is accompanied by a 2D image of the region to undergo surgery. A current or fictitious position of the surgical tool along the path may be indicated on the bar and/or on the 2D image. As the position of the tool is changed, other 2D images may be displayed, such that the surgical tool can be followed by the user.

These and other aspects of the invention are apparent from and will be elucidated with reference to the embodiments described hereinafter.

DETAILED DESCRIPTION OF THE INVENTION

In the following, the invention will be described by an exemplary embodiment related to neurosurgery using electrophysiological probes. The invention is however not limited to use with a neuro-EP system. Other surgical interventions where knowledge about anatomic information along a surgical trajectory (planned and/or navigated) is useful for clinical and/or diagnostic purposes may benefit as well from this invention. The invention may, e.g., be suitable for optical-needle guided interventions.

Figure 1:
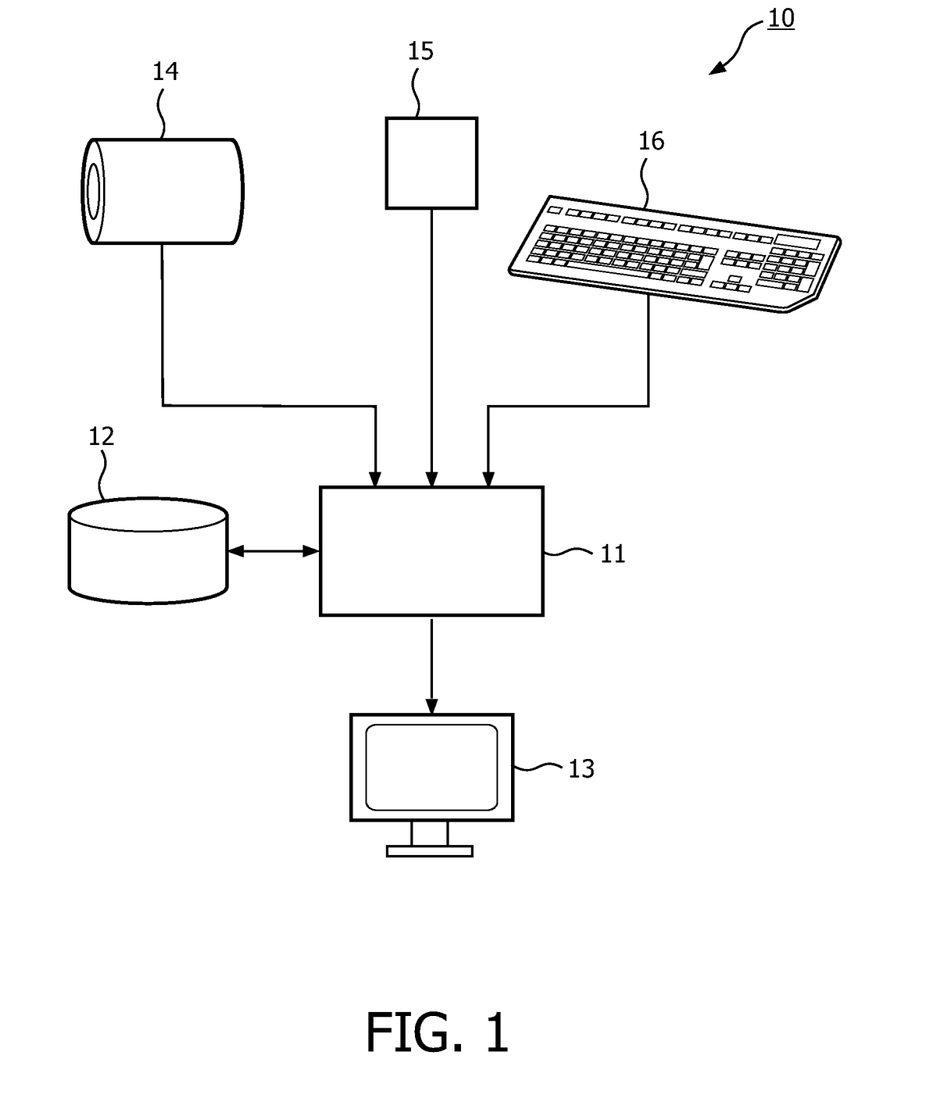
FIG. 1 schematically shows a system for visualizing a surgical path according to the invention.

FIG. 1 schematically shows a system 10 for visualizing a surgical path according to the invention. The system 10 comprises a processor 11 for receiving and processing all input data and providing a graphical representation of the surgical path as output data to a display 13. Input data, process parameters and output data may be stored on a memory 12. The processor 11, display 13 and memory 12 may together be part of one computer or may be separate items or parts of separate items. The input data for the processor 11 may come from different sources.

An image source 14, such as an MRI or CT scanner, may provide images of the anatomy of the region to undergo surgery. From the received images, the processor 11 may derive anatomical information about positions of anatomical structures in the corresponding region. Alternatively, the images or the anatomical information is provided to the processor 11 from a separate input source. The processor also uses geometric information describing the surgical path. This geometric information may be provided by a user via a user interface 16 or may be received from a separate path design system 15. The user interface 16 may, e.g., further be used for configuring several process parameters of the system 10 or for selecting display options for the display of the graphical representation of the surgical path. The user interface 16 may comprise all kinds of known user interface elements, such as a keyboard, pointing device, touch pad, touch screen or speech recognition system.

The surgical path may be computed by a computer using a path designing algorithm or designed by a surgeon or other person. The path may also be the result of a combination of computer algorithms and user modification.

Safety margins defining a desired minimum distance between the surgical tool and a critical anatomical structure may be provided together with the anatomical information describing the corresponding anatomical structure. Safety margins may also be pre-stored on the memory 12. Different anatomical structures and different types of anatomical structures may need different safety margins. Safety margins may be defined and/or modified by the user, e.g. via the user interface 16. In addition to the safety margins, the processor 11 may also use guidelines and/or restrictions for the use of the surgical tool as input for the visualization process.

Figure 2:
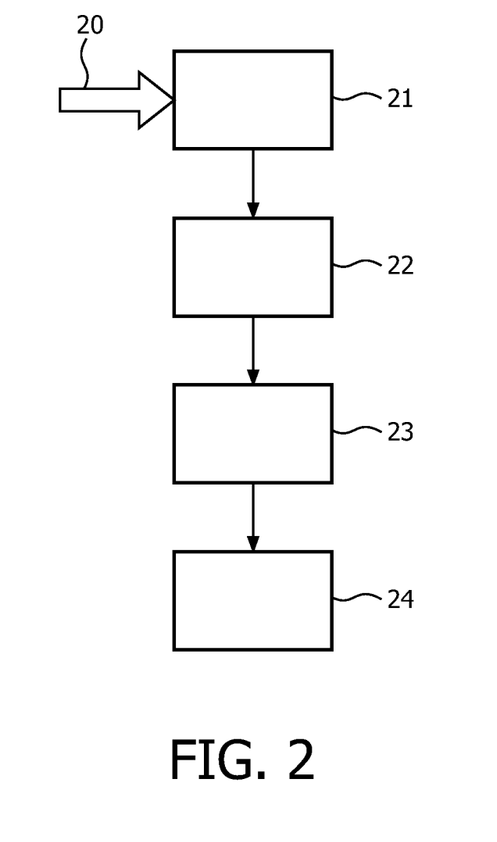
FIG. 2 shows a flow diagram of a method according to the invention.

The method to be performed by the processor 11 is schematically represented by the flow diagram of FIG. 2. In a data receiving step 21, the processor 11 receives all input data 20 that is used for visualizing a surgical path using the method of the invention. The input data 20 comprises geometric information describing the surgical path. It is to be noted that this geometric information may be received from a separate path designing process performed by the processor 11 itself. The input data 20 further comprises at least one safety margin. Safety margins may, e.g., be provided together with the anatomical information or set by a user via the user interface 16. Alternatively, the safety margin is already stored on the memory 12 and received therefrom. For example, the memory 12 may store a list of standard safety margins for different types of anatomical structures. The safety margin may further depend on other parameters, such as age, sex and weight of the subject of the surgery. The input data 20 also comprises anatomical information about a position of at least one anatomical structure in the region to undergo surgery. The anatomical information may be received as a list of structures and corresponding geometric coordinates defining their positions. Alternatively, the anatomical information is received in the form of images of the region to undergo surgery.

In an optional recognition step 22, image recognition techniques may be used for finding anatomical structures in the received images and for generating the required anatomical information.

In path segmenting step 23, the geometric information describing the surgical path and the anatomical information are compared and distances between the path and at least one anatomical structure are computed. The computed distances are compared to the safety margins. If for one or more segments of the surgical path, the distance to a nearby anatomical structure turns out to be smaller than the safety margin, then the segment is marked as a critical segment. Multiple safety margins may be used for indicating different safety levels. For example, safety margins of 1 mm, 2 mm and 3 mm may be used for indicating whether a trajectory comes 'unacceptably close', 'too close' or 'close', respectively.

Optionally, the path segmenting step 23 also takes into account guidelines and restrictions regarding the use of the surgical tool. For example, it may not be possible to take sharp corners or to take too many corners in a too small space. If the geometric information describing the surgical path indicates that a too guideline or restriction is violated, then the violating part of the surgical path is marked as a restricted segment.

In visualization step 24, a graphical representation of the surgical path is generated. The graphical representation may be 1D, 2D or 3D. The graphical representation may be displayed on a display screen, printed on paper or provided as output data suitable for display or print by an external display or printing device. In the generated graphical representation of the surgical path, the critical segments are highlighted. Optionally also the restricted segments are highlighted. The critical segments and the restricted segments are preferably highlighted differently, such that the user can easily see whether a safety margin or a tool restriction is violated.

Highlighting critical and/or restricted segments may be done in a lot of different ways. For examples, the highlighted segments may have a different color or shading than other parts of the surgical path. Alternatively, the path may be displayed wider or the special segment may be surrounded by a circle or other shape. Different segments may be highlighted differently. E.g. a color coding may be used for showing what kind of structure (e.g., blood vessel, nerve) is threatened or what kind of restriction is violated.

If at one position two or more safety margins and/or tool restrictions are violated, two highlighting methods may be combined. For example, half of the segment may get one color and the other half another color. Of course coloring the segment and surrounding it with a particular shape may also be combined. Alternatively, it may be decided to only visualize the most important violation. A more important violation may, e.g., be violating a safety margin for an anatomical structure which will cause large health risks when damaged. A more important violation may also be a tool restriction which makes it impossible to follow the path. The importance of a restriction may also depend on how much the safety margin or tool restriction is violated.

When highlighting segments, different color intensities may be used for indicating how much the safety margin or tool restriction is violated. If, e.g., the surgical path is green for the segments without any problem, segments with smaller problems (e.g. coming close to a blood vessel) may turn a little red and segments with bigger problems (e.g. cutting through a blood vessel) may be fully red. A trajectory coming pretty close to an important structure may have another color than a trajectory coming very close.

Figure 3:
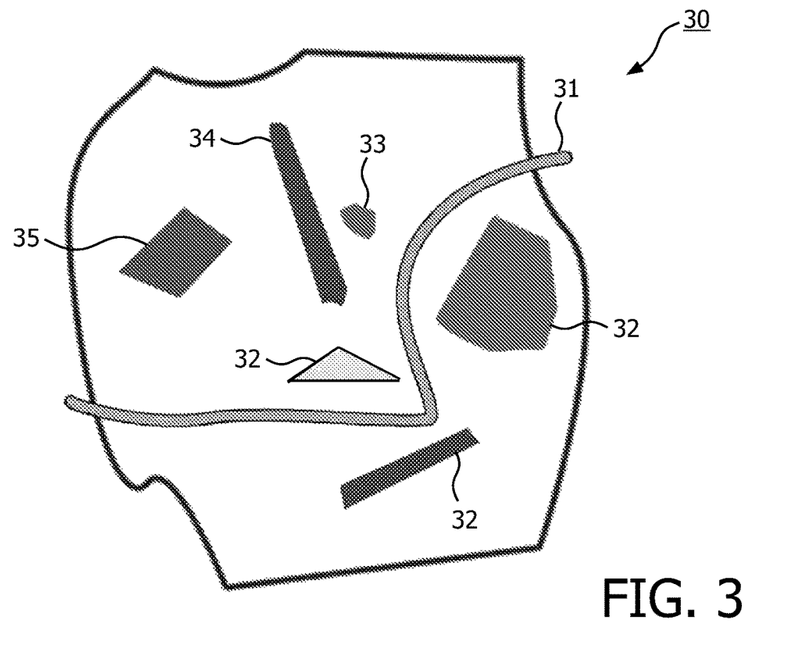
FIG. 3 shows an exemplary visualization of a surgical path.

FIG. 3 shows an exemplary visualization of a surgical path 31 in 2D. Together with the surgical path 31, some anatomical structures 32 which are close to the path 31 are displayed. The whole path 31 is visualized using only one color, because no safety margins are violated. Optionally, the safety margins could also be visualized. If each anatomical structure 32 has its own safety margin, the safety margins is preferably drawn around the anatomical structures 32. If all anatomical structures 32 have the same safety margin, it is also possible to draw the safety margin around the path 31. By adding safety margins to the figure, it is made very clear where the path 31 may come close to the safety margin.

Figure 4:
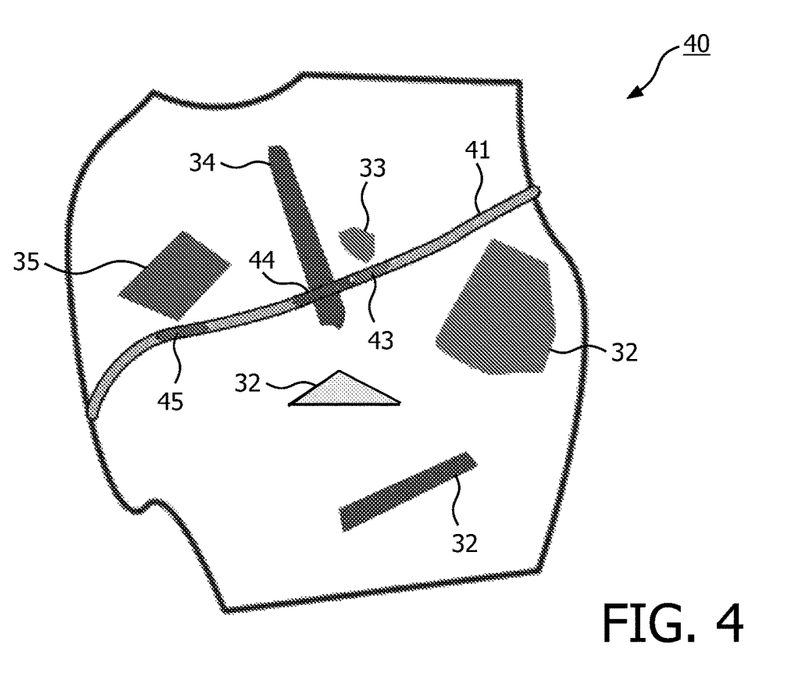
FIG. 4 shows an exemplary surgical path with highlighted critical segments.

FIG. 4 shows an exemplary surgical path 41 with highlighted critical segments 43, 44, 45. This figure is very similar to FIG. 3. The main difference with FIG. 3 is that the surgical path 41 comes within the safety margins of three anatomical structures 33, 34, 35. Two segments 43, 45 come too close to an anatomical structure 33, 35. One segment 44 even intersects an anatomical structure 34. The path segments 43, 44, 45 coming too close to or intersecting the respective anatomical structures 33, 34, 35 are highlighted by having a different color than the safe part of the surgical path 41. The critical segments 43, 44, 45 all have different colors, which may, e.g., represent the type of anatomical structure 33, 34, 35 being too close or which may indicate the severity of the health risk associated with the highlighted segment 43, 44, 45. The visualization of the surgical path as shown in FIG. 4 provides the surgeon with a very clear and intuitive overview of the problems to be expected.

Figure 5:
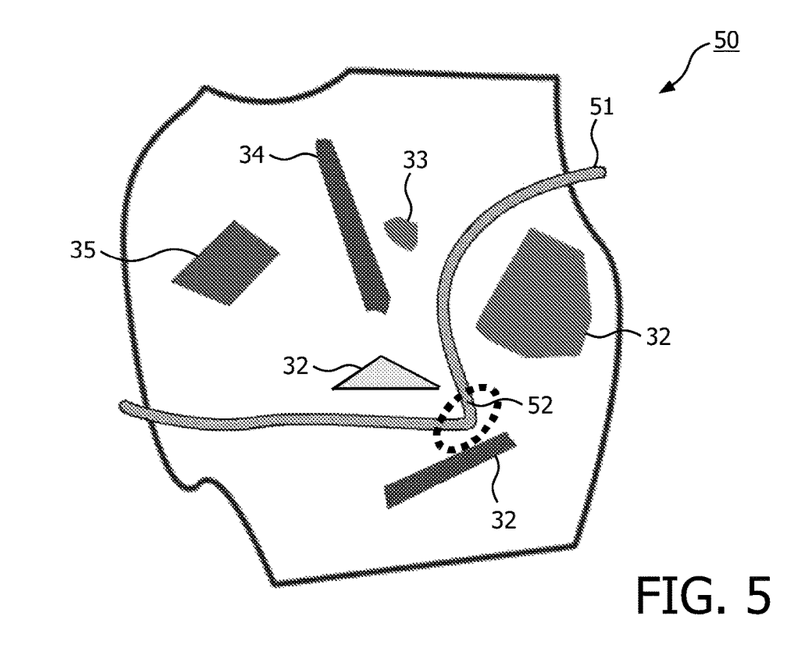
FIG. 5 shows an exemplary surgical path with a highlighted restricted segment.

FIG. 5 shows an exemplary surgical path 51 with a highlighted restricted segment 52. The segment 52 is highlighted by drawing an ellipse around it. The segment 52 is highlighted because a surgical tool restriction or guideline is violated at that part of the surgical path 51. At the highlighted segment, the surgical path 51 makes a sharp turn. This sharp turn may be too sharp for different reasons. E.g., it may cause too much tissue damage, there may be a risk of damaging the surgical tool or it may even be impossible for the surgical tool to make such a sharp turn.

Figure 6:
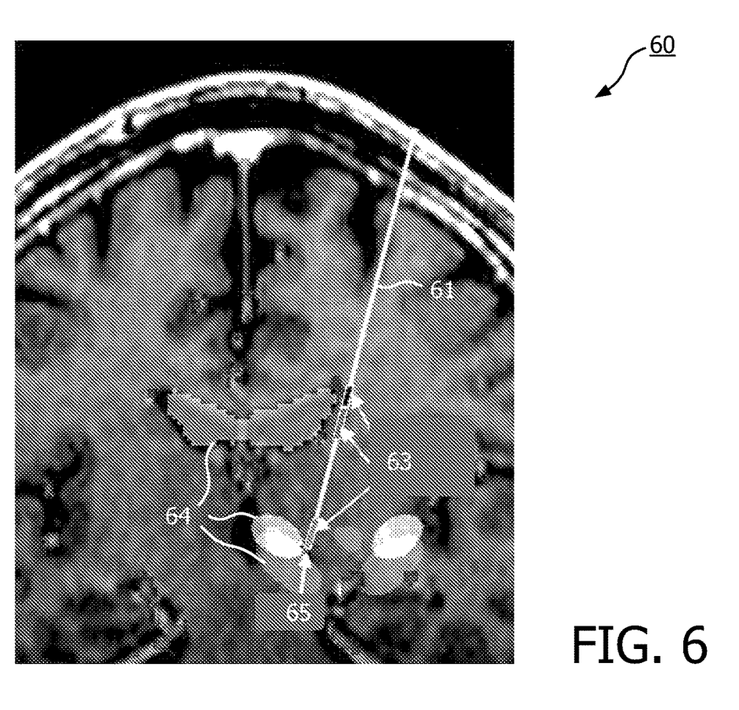
FIG. 6 shows an exemplary surgical path superimposed over an MRI image.

FIG. 6 shows an exemplary surgical path 61 superimposed over an MRI image 60 of brain. The surgical path 61 runs from an entry point to a target point 65 at which, e.g., tissue may be cut or removed, drugs may be delivered, neurons may be electrically stimulated or neurophysiological signals may be obtained. The image 60 shows a 2D slice of the brain. The surgical path 61 shown may completely lie in this 2D plane or may be projected onto this plane for making it possible to show the complete path 61. Just like the visual representations 31, 41, 51 of surgical paths in the previous figures, this figure may be used for planning a surgical trajectory 61 as well as for following a surgical tool during surgery. Similar to FIG. 4, FIG. 6 shows three highlighted path segments 63 which are too close (closer than the safety margin) to an anatomical structure 64.

Figure 7:
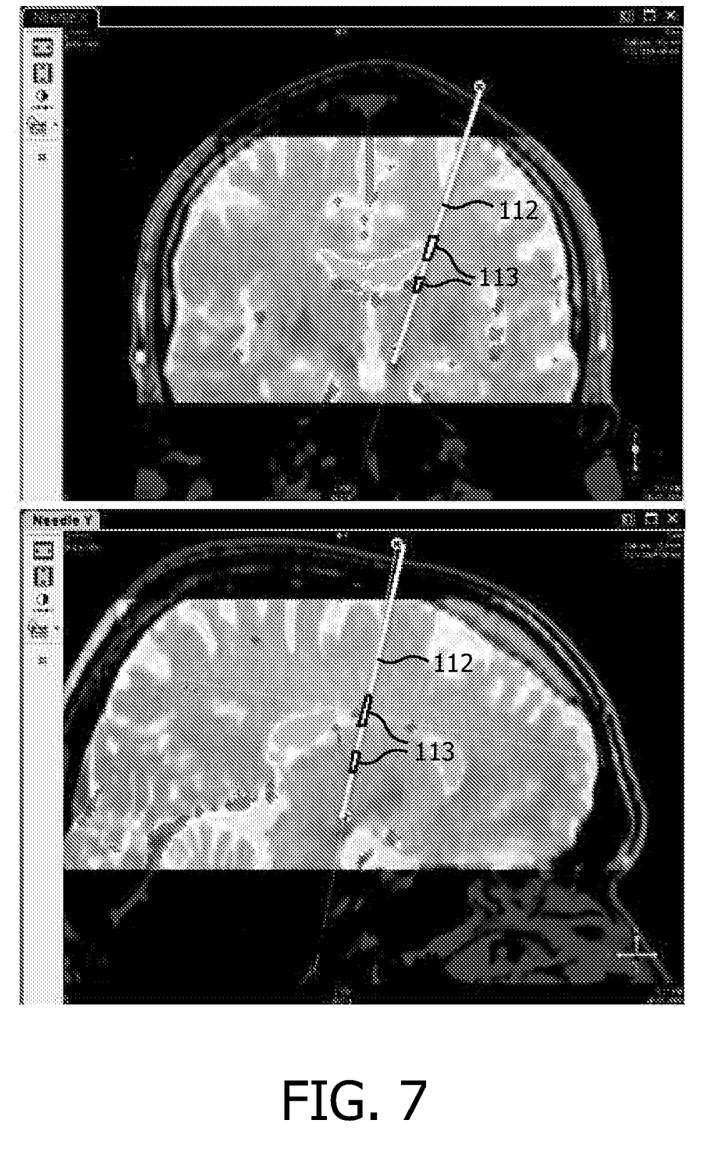
FIG. 7 shows an example of a visualization of a critical path.

FIG. 7 shows an example of a visualization of a critical path 112. In this visualization 112, two critical sections 113 are highlighted. At the critical section 113, the path 112 comes very close to important tissue which should not be damaged.

Figure 8:
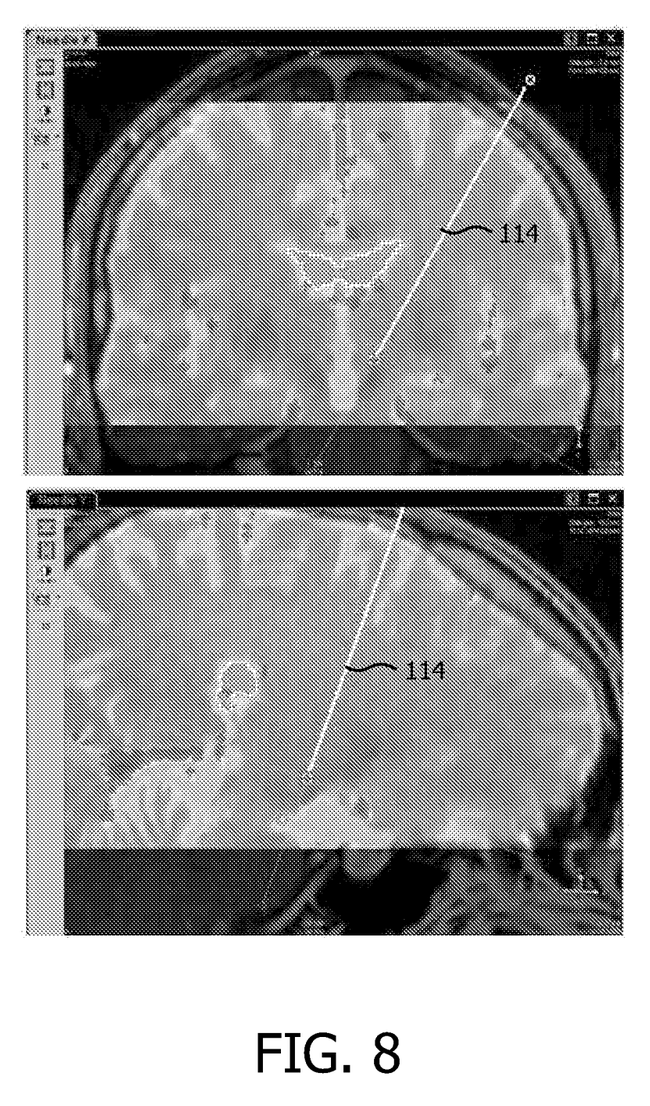
FIG. 8 shows an example of a visualization of a safe path.

FIG. 8 shows an example of a visualization of a safe path 114. This path 114 does not show any highlighted section, because it does not impose high risks upon critical structures.

Figure 9:
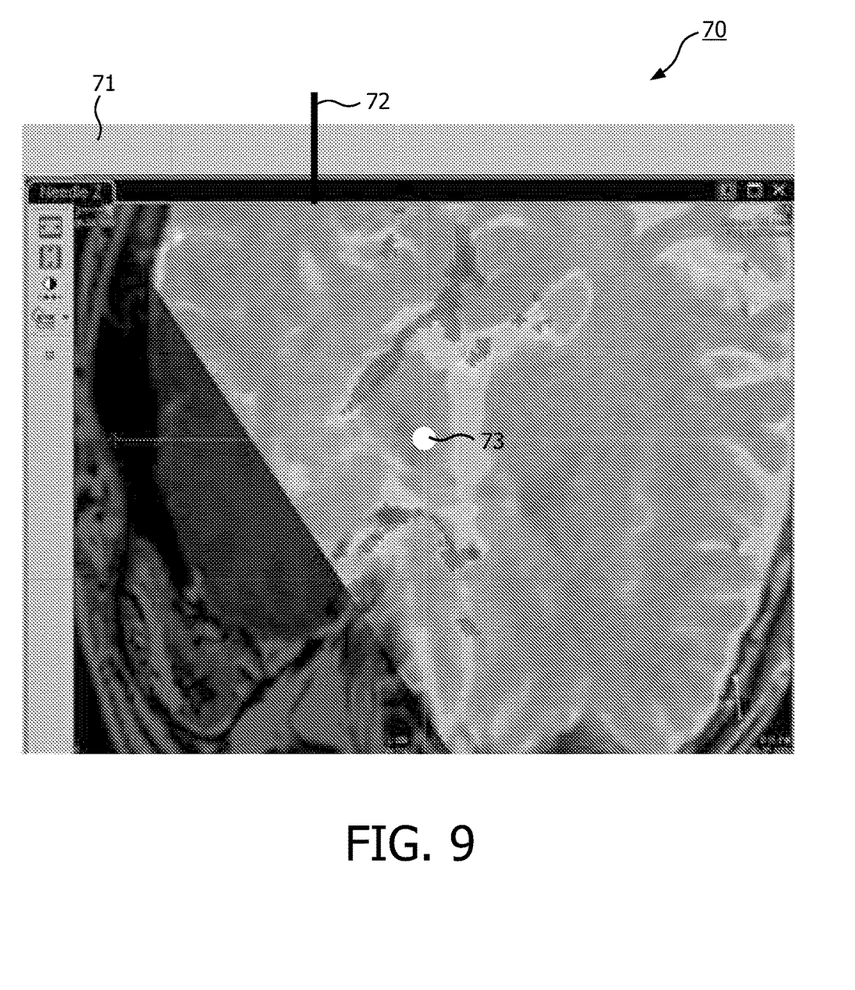
FIG. 9 shows an exemplary surgical path visualized as a bar next to an MRI image with the surgical tool at a safe position.

FIG. 9 shows an exemplary surgical path visualized as a bar 71 next to an MRI image 70 with the surgical tool at a safe position 73. The bar 71 is a one-dimensional visual representation of the surgical path. The bar 71 presents a simple overview of the problems and risks that may be associated with a particular trajectory. The bar 71 may either represent a section of the surgical path or the whole path from entry point to target point. A current position indicator 72 shows a relative position of the surgical tool. The image is a 2D image comprising and showing the position 73 indicated by the position indicator 72 on the bar 71. When the surgical tool is moved towards the target point, other 2D images will be shown such that the position 73 indicated in the image always corresponds to the position 72 indicated in the bar 71. The current position 72, 73 of the surgical tool may be a real position of the tool during surgery or an imaginary position during simulation or exploration of a planned surgical trajectory.

This embodiment makes it possible for the surgeon to simultaneously look at the anatomy of the region close to the surgical tool and at the risks and problems to be expected along the path. The surgical path displayed in FIG. 7-9 does not comprise critical or restricted segments. When exploring the path before surgery, the surgeon may use the bar 71 for quickly finding the images showing the anatomy in the region where problems are to be expected. During surgery, the highlighted segments of the bar 71 may make the surgeon aware of the risks at a certain position along the path while showing a detailed image of the region of the surgical tool.

Figure 10:
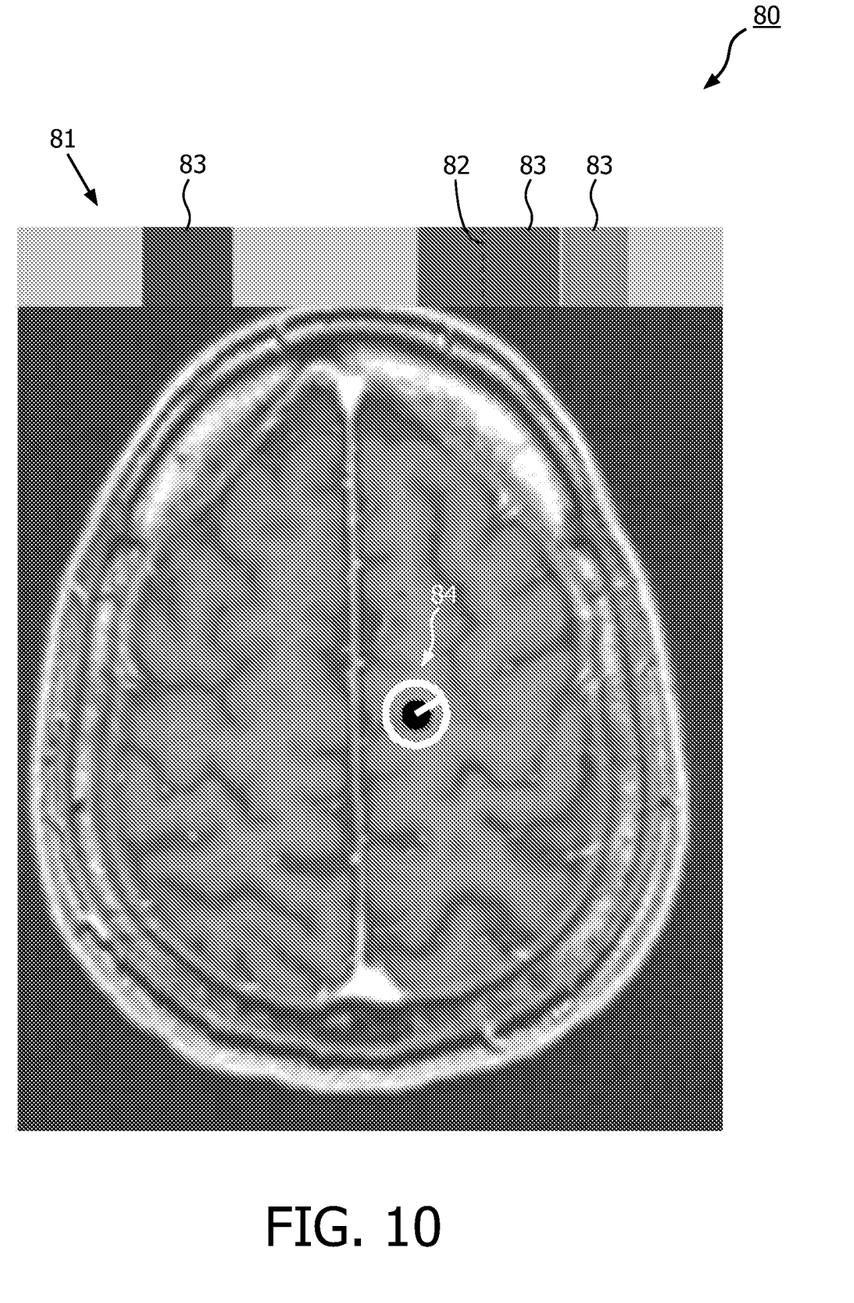
FIG. 10 shows an exemplary surgical path visualized as a bar next to an MRI image with the surgical tool at a critical position, and FIG. 11 schematically shows a close-up of a part of FIG. 10.

FIG. 10 shows an exemplary surgical path visualized as a bar 81 next to an MRI image 80 with the surgical tool at a critical position 82. This figure is very similar to FIG. 9. The main difference is that in FIG. 10 the path comprises three critical or restricted segments 83. The indicator 82 at the bar 81 is situated in a critical segment 83. The corresponding MRI image shows the current position 84 of the surgical tool together with information about the safety margin which is being violated at that position 84.

Figure 11:
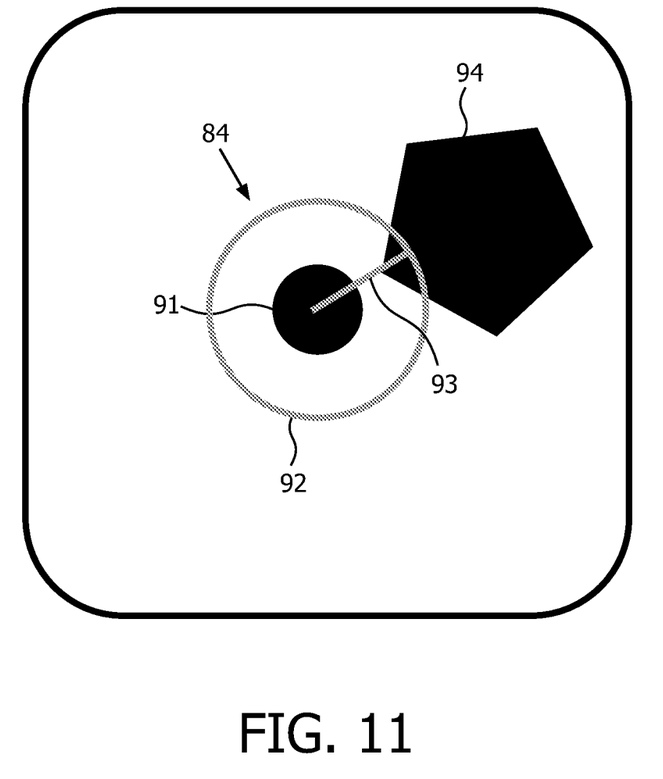

FIG. 11 schematically shows a close-up of the position indicator 84 in the MRI image of FIG. 10. The position indicator 84 shows a tool indicator 91 indicating the position of the surgical tool. The tool indicator 91 may show the tool dimension on scale, i.e. the tool indicator in the image exactly overlaps the anatomical structure which is also overlapped by the real surgical tool. To improve visibility, the tool indicator 91 for very small tools may be larger than in reality. The tool indicator 91 for larger tools may have a reduced size in order not to obscure too much of the image. Also the shape of the indicator may or may not reflect the shape of the real tool.

Around the tool indicator 91, a safety margin indicator 92 is shown. Because an anatomical structure 94 lies within the safety margin, the tool is now situated in a critical segment 83 which is also shown in the bar 81. A violation indicator 93 may indicate in which direction (seen from the tool) an anatomical structure 94 infringes the safety margin 92. In an alternative embodiment, the safety margin may be drawn around the anatomical structure and violation indicators may point towards the anatomical structures coming too close to the surgical tool.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method of visualizing a surgical path for a surgical tool, the method comprising:
   receiving:
   anatomical information about a position of at least one anatomical structure in a region to undergo surgery,
   geometric information describing the surgical path,
   at least one safety margin defining a minimal distance between the surgical tool and the anatomical structure, and
   at least one surgical tool restriction defining at least one geometric parameter for the surgical path necessary for a surgical tool to perform a procedure,
   defining a critical segment of the surgical path, the critical segment having a distance to the anatomical structure smaller than the safety margin,
   defining a restricted segment of the surgical path, in which the restricted segment of the surgical path does not meet the surgical tool restriction, and
   providing a graphical representation of the surgical path, wherein the critical segment and the restricted segment are highlighted on the graphical representation of the surgical path, wherein said critical segment and said restricted segment are highlighted differently from each other.

2. A method of visualizing a surgical path as claimed in claim 1, the method further comprising:
   receiving an image of a region to undergo surgery, and displaying the image together with the graphical representation of the surgical path.

3. A method of visualizing a surgical path as claimed in claim 2, further comprising using image recognition techniques for deriving the anatomical information from the image.

4. A method of visualizing a surgical path as claimed in claim 2, wherein the graphical representation of the surgical path is aligned with and displayed upon the image of the region to undergo surgery.

5. A method of visualizing a surgical path as claimed in claim 1, wherein the graphical representation of the surgical path comprises a bar, both ends of the bar representing a first point and a second point on the surgical path, a position on the bar in between the ends representing a corresponding position on the surgical path in between the first point and the second point.

6. A method of visualizing a surgical path as claimed in claim 5, the first point being a start point of the surgical path, the second point being a target point of the surgical path.

7. A method of visualizing a surgical path as claimed in claim 1 wherein the graphical representation further shows the safety margin.

8. A method of visualizing a surgical path as claimed in claim 1, wherein the critical segment is highlighted using a color coding, a color of the segment representing the anatomical structure.

9. A method of visualizing a surgical path as claimed in claim 8, wherein an intensity of the color of the segment represents a closeness of the surgical path to the safety margin.

10. A method of visualizing a surgical path as claimed in claim 1, further comprising receiving a current position of the surgical tool during the surgery and wherein the graphical representation further shows the current position.

11. A non-transitory computer readable storage medium comprising a non-transitory computer readable program product, wherein the computer readable program product when executed on a computer causes the computer to perform the steps of claim 1.

12. A system for visualizing a surgical path for a surgical tool, the system comprising,
  an input for receiving:
  anatomical information about a position of at least one anatomical structure in a region to undergo surgery,
  geometric information describing the surgical path,
  at least one safety margin defining a minimal distance between the surgical tool and the anatomical structure, ands
  at least one surgical tool restriction defining at least one geometric parameter for the surgical path necessary for a surgical tool to perform a procedure,
  a processor configured to define a critical segment of the surgical path, the critical segment having a distance to the anatomical structure smaller than the safety margin and a restricted segment of the surgical path, in which the restricted segment of the surgical path does not meet the surgical tool restriction, wherein the processor is further configured to generate a graphical representation of the surgical path wherein the critical segment and the restricted segment are highlighted differently from each other on the graphical representation of the surgical path, and
  an output for providing the graphical representation.

\* \* \* \* \*